United States Patent [19]
Huber

[11] Patent Number: 5,976,512
[45] Date of Patent: *Nov. 2, 1999

[54] SYMETRICAL HYDROXYPHENYL-S-TRIAZINE COMPOSITIONS

[75] Inventor: Ulrich Huber, Erlenbach, Switzerland

[73] Assignee: Roche Vitamins Inc., Parsippany, N.J.

[*] Notice: This patent issued on a continued prosecution application filed under 37 CFR 1.53(d), and is subject to the twenty year patent term provisions of 35 U.S.C. 154(a)(2).

[21] Appl. No.: 09/034,616

[22] Filed: Feb. 17, 1998

[30] Foreign Application Priority Data

Mar. 3, 1997 [EP] European Pat. Off. .............. 97103434

[51] Int. Cl.$^6$ .............................. A61K 7/42; A61K 7/00; A61K 31/53
[52] U.S. Cl. .............................. 424/59; 424/60; 424/400; 424/401; 514/241
[58] Field of Search .............................. 544/216

[56] References Cited

U.S. PATENT DOCUMENTS 3,896,125  7/1975  Helmo et al. .................. 260/249.5
5,185,445  2/1993  Meuwly et al. .................. 544/216

FOREIGN PATENT DOCUMENTS 484 695  3/1970  Switzerland .

OTHER PUBLICATIONS

Abstract of Swiss Patent No. CH 484 695 (1963).

Primary Examiner—Shelley A. Dodson
Attorney, Agent, or Firm—Mark E. Waddell; Stephen M. Haracz; Bryan Cave LLP

[57] ABSTRACT

The invention is concerned with compounds of formula I:

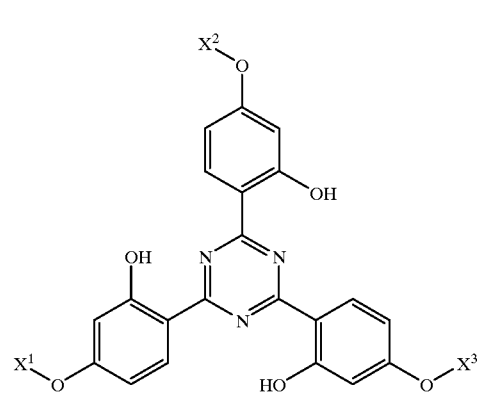

which are useful as sun screening agents.

52 Claims, No Drawings

SYMETRICAL HYDROXYPHENYL-S-TRIAZINE COMPOSITIONS

BACKGROUND OF THE INVENTION

Sunlight accelerates skin aging and even causes skin cancer, with these undesired effects being caused not only by UV-B radiation, but primarily by the UV-A radiation with wavelengths in the region of about 320 to 400 nm, which directly tans the skin.

It is already known from Swiss Patent 484 695 that the symmetrical tris-(2,4-dihydroxyphenyl)-1,3,5-triazines are very efficient UV-A/B light screening agents for the protection of textiles. A substantial disadvantage is, however, the extremely poor solubility of this class of compounds in practically all solvents, which does not permit them to be used, e.g., for cosmetic applications.

o-Hydroxyphenyl-s-triazines, which absorb UV light, are described in U.S. Pat. No. 3,896,125, but they are insoluble or soluble only with difficulty in non-polar polymers such as polyethylene, polypropylene or polyester resins.

Further, 2-hydroxyphenyl-s-triazines having a silicon-containing residue in in the 4-position of the 2-hydroxyphenyl group for the light stabilization of organic polymers are known from EP-A1-502821. In dimensionally stable articles produced from polymers stabilized therewith, the UV absorber contained in the outer layers of the article prevents the penetration of short-wave light which is especially harmful for polymers, i.e., primarily of UV-B radiation, into the interior of the article.

However, there exists the pressing need, especially for the producers of body care products, to make the hydroxyphenyl-s-triazine class of compound, having regard to its light screening action, also available for other purposes. Therefore, at least a good solubility in organic solvents, especially in cosmetic solvents, and a good photostability are required.

SUMMARY OF THE INVENTION

It has now been found that compounds of the formula:

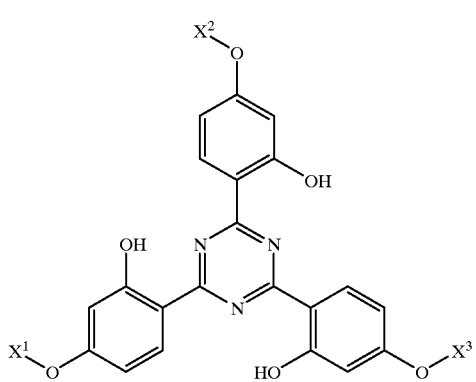

I wherein:

$X^1$, $X^2$ and $X^3$ are independently —Z—S or two of X1, $x^2$ and $X^3$ are are —Z—S and the third is H or S, Z is a saturated or mono- or multipli- unsaturated alkyl group, either linear or branched, having 3–12 carbon atoms, and S is tri-$C_{1-6}$-alkyl-silyl, tri-$C_{1-6}$-alkoxy-silyl or triphenyl-silyl, where the $C_{1-6}$-alkyl or $C_{1-6}$-alkoxy groups may be the same or different, or an oligosiloxane having 1–8 silicon atoms and 3–15 carbon atoms, are useful as light screening agents.

DETAILED DESCRIPTION OF THE INVENTION

As used herein, S is a silyl group which is further elaborated, below. When $X^1$, $X^2$ and $X^3$ are —Z—S, they are preferably all the same. When two of $X^1$, $X^2$ and $X^3$ are —Z—S and the third is S, the two that are —Z—S are preferably the same.

The compounds of the invention can be dissolved well in organic solvents, especially in cosmetic solvents, and are excellent UV-A filters in that, with outstanding skin compatibility and stability (light, heat, moisture), they bring about a strong reduction in the stress effect on the skin and thus retard skin aging, i.e., they are substances which absorb the erythema-producing UV-A radiation in the region of about 320–400 nm. In particular, however, the compounds of the invention are UV-A filters which also have an outstanding photostability. Accordingly, they can be used in cosmetic emulsions and give preparations which are simple to process and which are outstandingly suitable for applications as cosmetic sunscreen agents to the skin or in hair care agents.

Preferably, the spacer groups Z have 2–6 carbon atoms between the oxygen and the silicon residue S. Products in which the spacer groups Z have 2 or 3 carbon atoms between the oxygen and the silicon residue S may be prepared from inexpensive starting materials. Products in which Z contains 4–6 carbon atoms between the oxygen and S need less purification, since a side-reaction which occurs when Z has 2 or 3 carbon atoms between the oxygen and S occurs to a much less extent.

Examples of spacer groups Z are 3-propyl, 2-propyl, 3-propenyl, 2-propen-3-yl, 2-propen-2-yl, 2-methyl-2-propyl, 2-methyl-3-propenyl, 4-butyl, 3-butyl, 2-butyl, 3-butenyl, 3-methyl-2-butyl, 2,4-pentadien-5-yl, 4-pentyl, 5-pentyl, 5-hexyl, 6-hexyl and 2-dodecen-12-yl. Preferred groups Z are 3-propyl, 3-propenyl, 2-propen-2-yl, 4-butyl, 5-pentyl, and 6-hexyl.

Examples of silyl groups S are $SiMe_3$, $SiEt_3$, $SiMe_2$ethyl, $Si(n\text{-propyl})_3$, $Si(isopropenyl)_3$, $Si(\text{tert. butyl})_3$, $Si(\text{sec. butyl})_3$, $SiMe_2\text{tert.butyl}$, $SiMe_2\text{sec.butyl}$, $SiMe_2\text{thexyl}$, (thexyl is 1,1,2-trimethylpropyl), $Si(OMe)_3$, $Si(OEt)_3$, $Si(OPh)_3$, or oligosiloxane. As used herein Me=methyl, Et=ethyl and Ph=phenyl.

Any conventional oligosiloxane may be used in accordance with the present invention as the group S. Preferred oligosiloxanes are —$SiMe_m(OSi\ Me_3)_n$ wherein m=0, 1 or 2, n=3, 2 or 1 and m+n=3 and groups of the formulae:

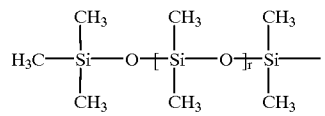

and

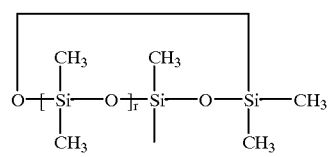

wherein r is an integer from 0 to 6.

The preferred groups S are $SiEt_3$, $SiMe_2$ethyl, $Si(n\text{-propyl})_3$, $SiMe_2\text{tert.butyl}$, $SiMe_2\text{thexyl}$, $Si(OEt)_3$, $Si(OSiMe_3)_3$, $Si(Me)(O\text{—}SiMe_3)_2$, and $Si(Me)_2(O\text{—}SiMe_3)$.

The necessary presence of three hydroxy groups in the ortho-position to the triazine appears to be an essential feature for the pronounced UV-A filter effect. Some examples of compounds in accordance with the invention are set forth hereinafter (Table I).

TABLE 1

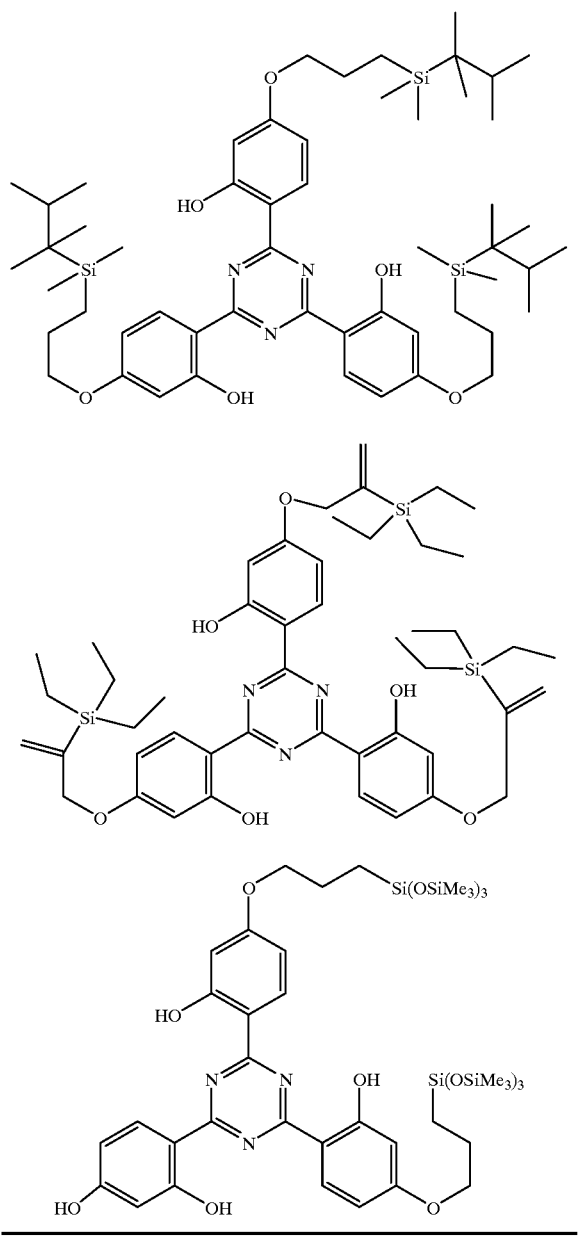

The compounds in accordance with the invention are colourless or light yellowish, liquid, crystalline or semi-liquid substances. They are distinguished by high photostablilty, good solubility in organic solvents, especially cosmetic solvents, and a short and economical synthetic route.

The compounds in accordance with the invention have a pronounced absorption maximum in the UV-A region. In addition, a substantially smaller second UV absorption maximum is present in the UV-B region, and accordingly these substances can also be used simultaneously to protect against both harmful UV regions.

However, in order to obtain a so-called A+B total block, which protects the skin from premature aging and in many cases from light-initiated dermatoses, it is often advantageous or useful to include other UV filters in the same formulation, especially other UV-B filters.

The invention is also directed to light screening compositions for topical application which comprise a compound of the invention dispersed in a carrier which is acceptable for topical application. The production of novel light screening compositions, especially of preparations for skin protection and, respectively, sunscreen preparations for everyday cosmetics, comprises incorporating a compound of the invention in a cosmetic base which is conventionally used for light screening agents. The concentration of the compound of the invention in the preparation is not critical, so long as a measurable amount of light screening is achieved in accordance with conventional methods of measuring light screening. Where convenient, other conventional UV-A, and respectively, UV-B filters may also be combined during this incorporation. In order to achieve especially high light screening factors, it is often advantageous to use several different UV filters in such a composition.

Such UV-A filters are, for example:
1-(4-Methoxyphenyl)-3-(4-tert.-butylphenyl)propane-1,3-dione (also known as butylmethoxydibenzoylmethane), trade name Parsol® 1789, [sold by F. Hoffmann-La Roche AG, Basel],
4-isopropyl-dibenzoylmethane,
2,2'-dihydroxy-4-methoxybenzophenone (also known as dioxybenzone or benzophenone-δ),
2-hydroxy-4-methoxybenzophenone-5-sulphonic acid (also known as sulisobenzone, benzophenone-4),
2-hydroxy-4-methoxybenzophenone (also known as oxybenzone, benzophenone-3),
3,3,5-trimethyl-cyclohexyl N-acetyl-anthranilate (also known as homomenthyl N-acetyl-anthranilate), and
2-methylanthranilate.

As UV-B filters, i.e., as substances with absorption maxima between about 290 and 320 nm, there can be mentioned usual UV-B filters such as, for example, the following organic compounds which belong to the most varied classes of substance:
1) p-Aminobenzoic acid derivatives, such as, e.g, ethyl p-aminobenzoate and other esters, such as propyl, butyl, isobutyl p-aminobenzoate, ethyl p-dimethylaminobenzoate, glyceryl p-aminobenzoate and amyl p-aminobenzoate,
2) cinnamic acid derivatives, such as, e.g., 2-ethoxyethyl p-methoxycinnamate, 2-ethylhexyl p-methoxycinnamate, p-methoxycinnamate acid ester mixtures and cinnamic acid ester mixtures,
3) dibenzalazine,
4) heterocyclic nitrogen compounds such as 2-phenylbenzimidazole derivatives, e.g. 2-phenylbenzimidazole-5-sulphonic acid,
5) salicylic acid derivatives, e.g., menthyl salicylate, homomenthyl salicylate and phenyl salicylate,
6) benzophenone derivatives, e.g., 4-phenylbenzophenone, isooctyl 4-phenylbenzophenone-2-carboxylate and 2-hydroxy-4-methoxybenzphenone-5-sulphonic acid,
7) coumarin derivatives, e.g., 7-oxycoumarin, β-umbelliferoneacetic acid and 6,7-dioxycoumarin,
8) gallic acid derivatives, e.g., digalloyl trioleate,
9) arylidenecycloalkanones, e.g., benzylidenecamphor,
10) anthranilic acid derivatives, e.g., menthyl anthranilate,
11) hydroxyphenylbenztriazole.

Especially suitable for an effective UV absorption are also metal oxide pigments such as, e.g., titanium oxide, zinc oxide, cerium oxide, zirconium oxide, iron oxide and their mixtures, which have an average particle size diameter of about ≦100 nm, which can be mixed very well with the filter-effective compounds of the invention and which are likewise very effective together with the previously named filters.

As cosmetic bases usual for light screening agents in the scope of the present invention there can be used any conventional preparation which corresponds to the cosmetic requirements, e.g., conventional creams, lotions, emulsions, salves, gels, sprays, sticks, milk and the like. The light screening effect also depends, of course, on the base which is used. Further, in the case of the same base the intensity of the light screening effect depends on the active substance concentration. Suitable concentrations lie, e.g., between 1–6%, preferably between 1.5–4%, of a compound of of the invention in the cosmetic preparation. The ratio of a compound of the invention to UV-B filter, which may also be incorporated, is not critical.

Having regard to their good lipophility, the compounds of the invention can be incorporated well into oil-containing and fat-containing cosmetic preparations.

With respect to the lipophility, the compounds of the invention in accordance with the invention are superior to the substituted triazines referred to earlier in that all compounds of the invention fulfil the criteria which are required in the present instance, namely a high solubility in cosmetic solvents such as, isopropyl myristate (e.g., DELTYL EXTRA, [Givaudan Roure Vernier, Switzerland]), PPG 15-stearyl ether (e.g., ARLAMOL E, [ICI Surfactants Everberg 1 Belgium]), cocoyl capylate/caprate (e.g., CETIOL LC, [sold by Henkel KGaA, Düsseldorf Germany]) or diisopropyl adipate (e.g., CRODAMOL DA, [Croda Universal Ltd., North Humberside, England]), as the compounds of the invention set forth hereinafter by way of example and their solubilities in CETIOL LC and/or in CRODAMOL DA show (Table II).

TABLE II

| | Solubility in % CETINOL LC | Crodamol DA |
|---|---|---|
| [structure 1] | >20% | |
| [structure 2] | 6.7% | 7.1% |

TABLE II-continued
| | Solubility in % CETINOL LC | Crodamol DA |
|---|---|---|
| 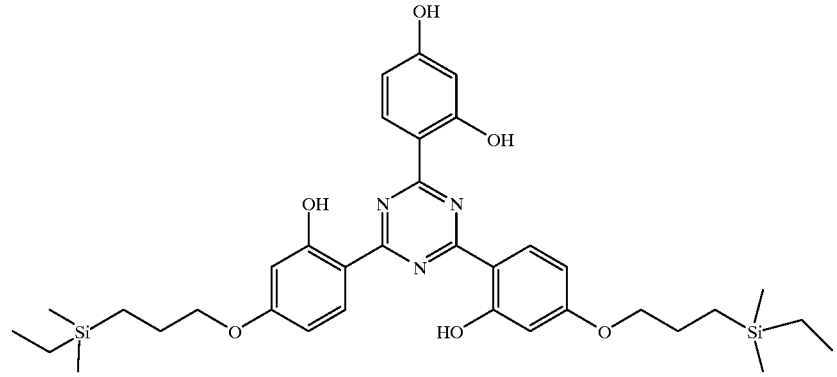 | 1.6% | 4.9% |
| 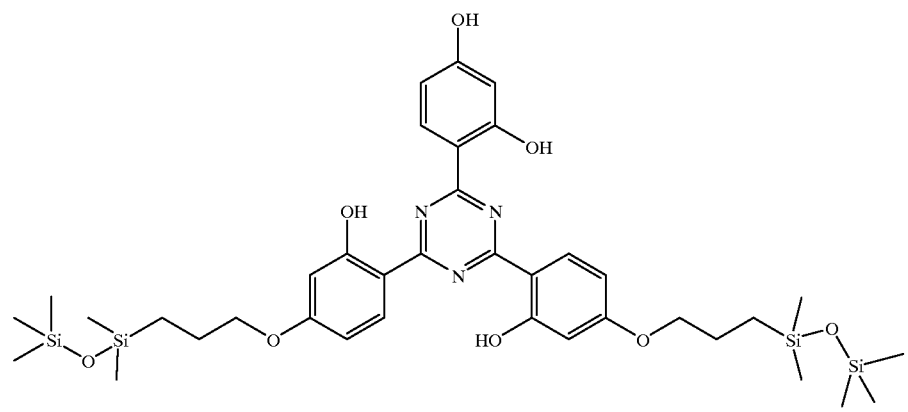 | 1.3% | 3.1% |
| 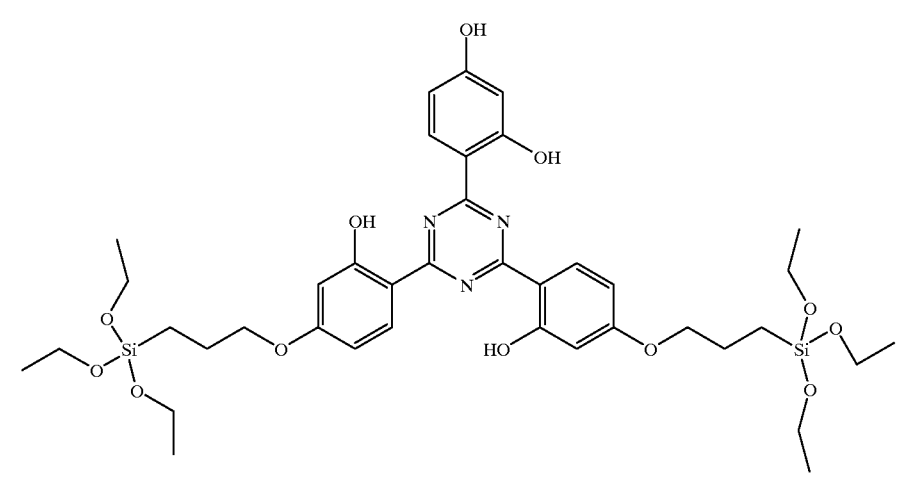 | | 4.3% |

TABLE II-continued
| | Solubility in % CETINOL LC | Croda-mol DA |
|---|---|---|
| 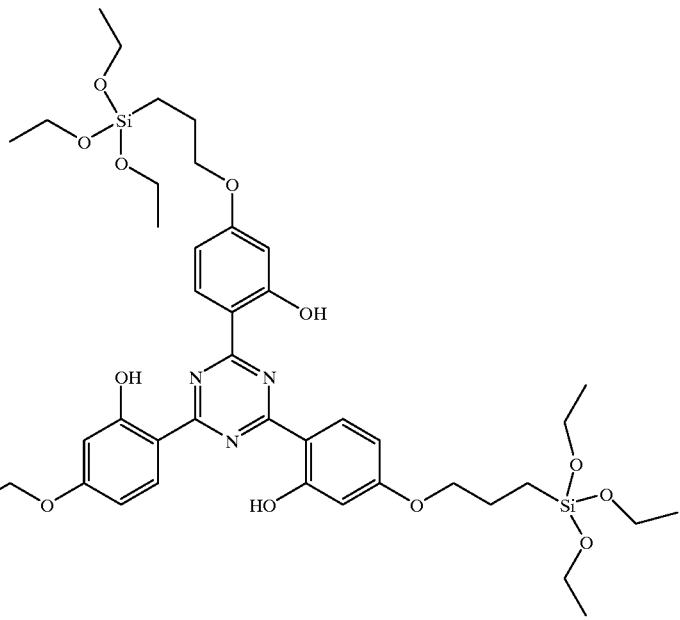 | 14% | >34% |
| 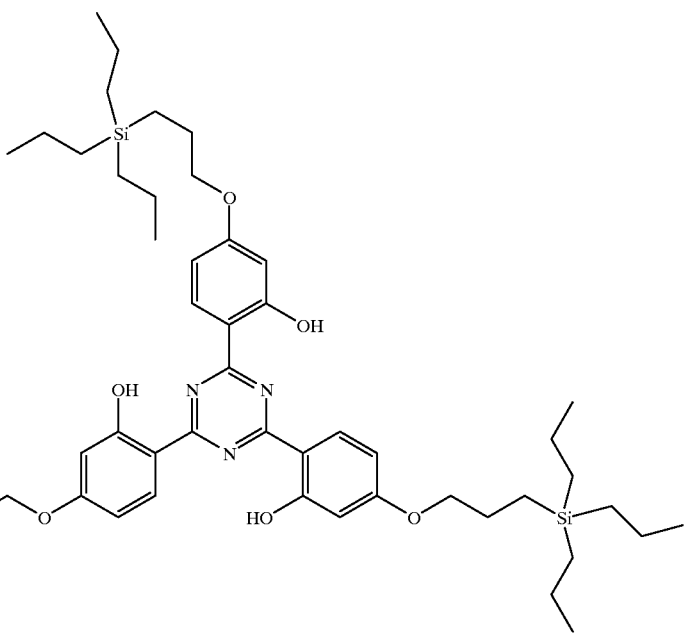 | 14% | 18% |

TABLE II-continued
| | Solubility in % CETINOL LC | Croda-mol DA |
|---|---|---|
| 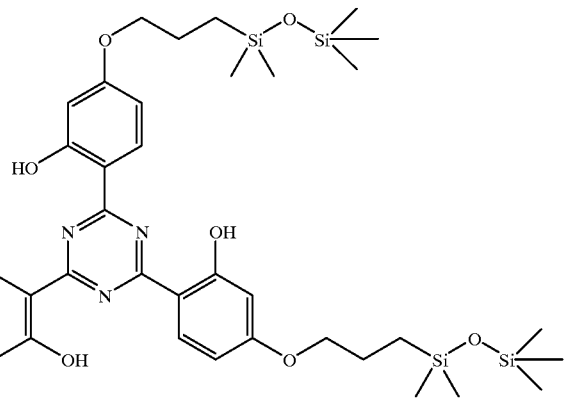 | >10% | |
| 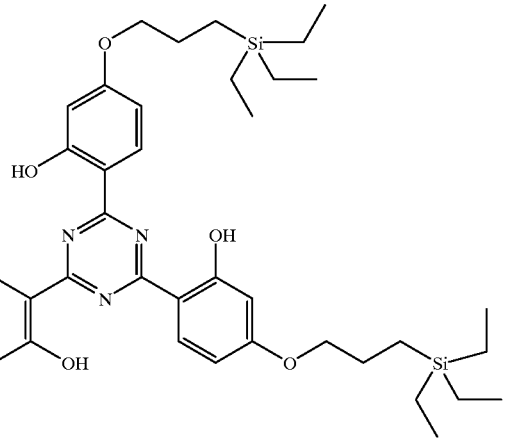 | >10% | |
| 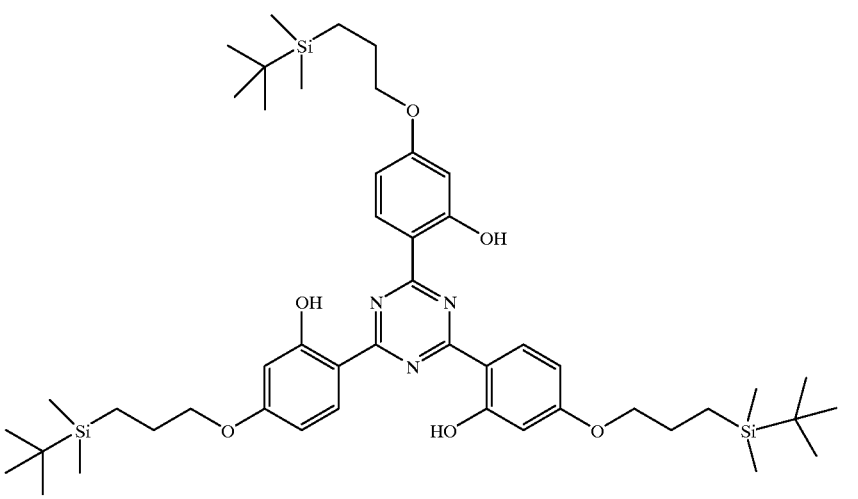 | 5.2% | 4.6% |

TABLE II-continued

| | Solubility in % CETINOL LC | Crodamol DA |
|---|---|---|
| | | 1.5% |

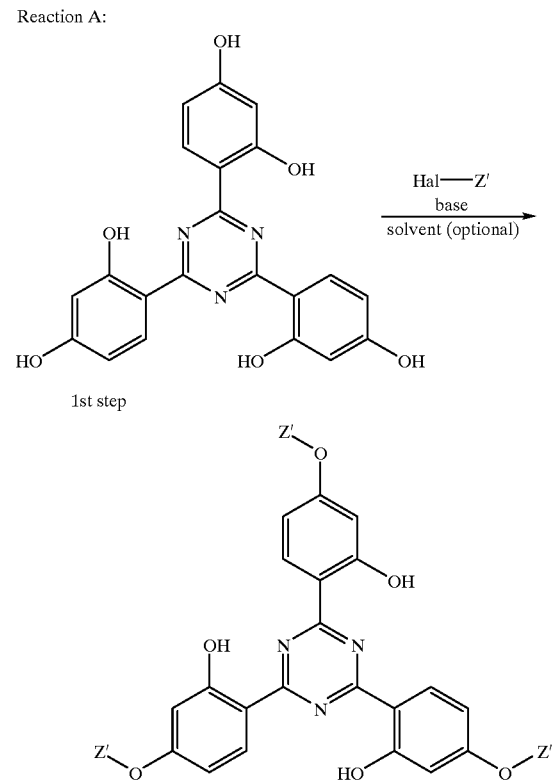

On the other hand, in the case of the prior art structures, solubilities of only 0.5% or less are achieved in these two solvents. The precursors of the above compounds dissolve in CETIOL LC to less than 0.05%.

The compounds of the invention are therefore especially suitable for cosmetic uses, since they have not only a high solubility in cosmetic solvents, but also an outstanding UV-A filter effect.

From Table II it will also be evident that, in the case of the same spacer group Z, the solubility in the cosmetic solvents depends critically on the silicon residue S, with compounds of the invention in which one or more $OSiMe_3$ or three OEt or three alkyl groups larger that methyl are substituted on the Si have the highest solubilities, and therefore such compounds of the invention are preferred for use in light screening agents.

The invention is accordingly concerned with the novel compounds of the invention, their manufacture, light screening compositions, namely light screening preparations for cosmetic purposes containing compounds of the invention, preferably also in combination with a UV-B filter, and the use of the compounds of the invention as light screening agents, especially for cosmetic purposes.

The synthesis of the compounds of the invention is possible in a simple and economical manner and can be illustrated as follows.

Reaction A:

1st step

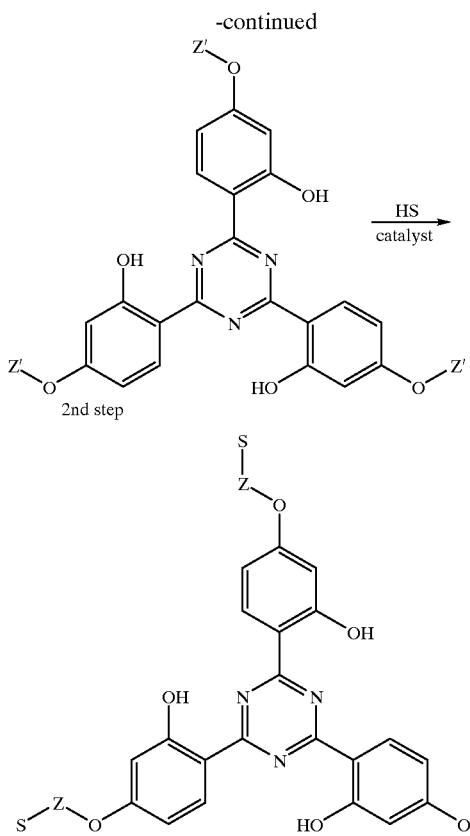

2nd step

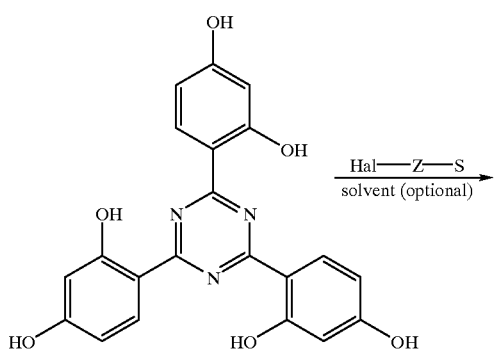

Starting from symmetrical tris-(2',4'-dihydroxyphenyl)-1,3,5-triazine, in a first step by reaction with a species Z' provided with a leaving group, e.g., with a halogenated species Hal-Z', as shown above in Reaction A, in the presence of a base, the hydroxyphenyl groups in the 4-position are substituted by the spacer Z', on which thereupon in a second step the compound I in accordance with the invention is formed by hydrosilylation with Si—H bonds. In this case, Z' differs from Z in that Z' contains one stage of unsaturation more than Z. Thus, when, e.g., Z contains a double bond then Z' contains a triple bond or two double bonds.

The reaction can, however, also be carried out in only one step when the species provided with a leaving group already contains the silicon residue S, i.e., for example, when Hal-Z—S is used in place of Hal-Z', as shown in Reaction B.

Reaction B:

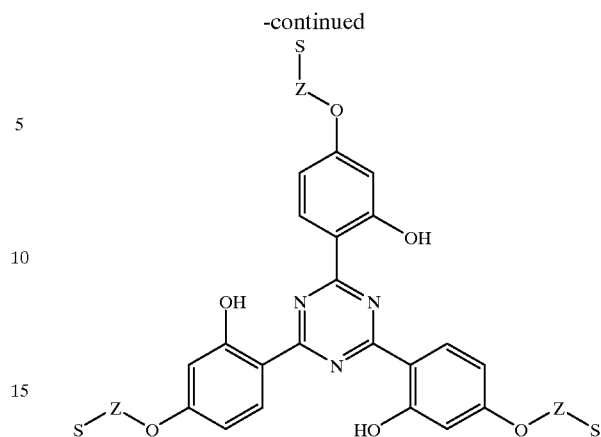

The one stage manufacture of the compounds of formula I is more cost effective and is therefore preferred. However, both Reaction A and B often do not take place completely or the spacer groups Z are lost during the reaction, so that after the reaction only parts of compounds of the formulae:

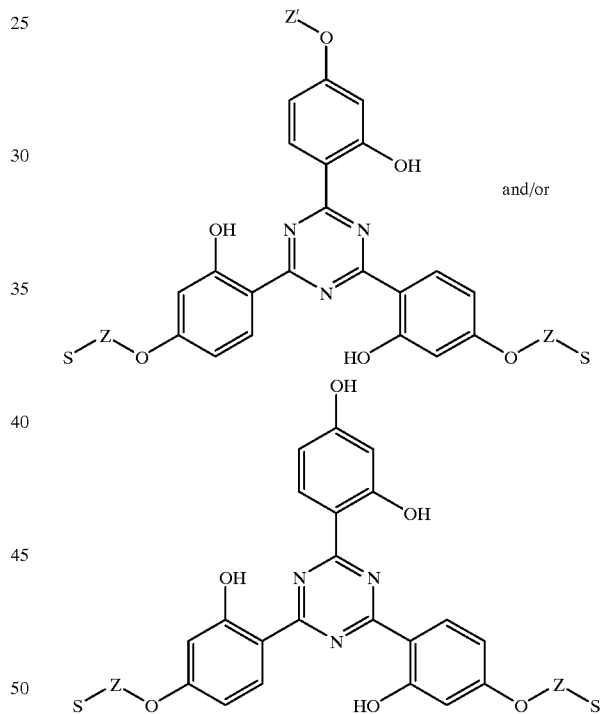

are present.

Inorganic bases such as, e.g., KOH, NaOH or NaH or alcoholates such as, e.g., Na methylate, Na ethylate or K tert.butylate or amines such as, e.g., triethylamine, pyridine, diazobicyclononane or p-dimethylaminopyridine or amides such as, e.g., Li diisopropylamide can be used as bases.

Suitable solvents for the first step of Reaction A and, respectively, for the one-step access (Reaction B) are conventional solvents, especially polar solvents such as alcohols, e.g., ethanol, isopropanol, methoxyethanol or propylene glycol, or also THF, water, pyridine, DMSO or DMF.

Suitable catalyst are homogeneous Pt catalysts, e.g., Pt-divinyl-tetramethyl-disiloxane or chloroloplatinic acid or metallic platinum, e.g., Pt/C. In place of Pt there can also be used other transition metal catalysts in heterogeneous form or in homogenous form as complexes, such as, e.g., Mo, Ru, Rh, Pd, Cr, Fe, Co, Ni or Cu. Rhodium salts or complexes such as, e.g., rhodium(II) acetate dimer, bis-(1,5-cyclooctadiene)-dirhodium(I) dichloride, tris-(triphenylphosphine)-rhodium(I) dichloride and polymer-bound tris-(triphenylphosphine)-rhodium(I) dichloride are especially suitable. Here the reaction is carried out either without a solvent or in solvents, e.g., toluene, xylene, pyridine, THF, dioxan, dichloroethane or methylene chloride.

Further advantages, features and particulars will be evident from the following Examples.

EXAMPLE 1

Introduction of triethyl-silane into 5,5',5'-tris-allyloxy-2,2',2"-[1,3,5]-triazine-2,4,6-triyltris-phenol to give 5,5',5"-tris-(3-triethylsilyl)-propyloxy-2,2',2"-[1,3,5]-triazine-2,4,6-triyl-tris-phenol 1.74 g (3 equiv.) of triethyl-silane (Fluka) are added dropwise to a suspension of 2.63 g of 5,5',5"-tris-allyloxy-2,2',2"-[1,3,5]-triazine-2,4,6-triyl-tris-phenol, prepared according to Swiss Patent 484 695, in 35 ml of toluene under Ar protective gas, treated with a few drops of platinum-divinyl-tetramethyl-disiloxane solution (ABCR GmbH) and heated to 80° C. for 100 hours. The cooled solution is thereupon washed with moist methanol and concentrated to give 3.7 g of a honey-like crude product which, for identification, is chromatographed in hexane over silica gel. Yield 40% of theory of a yellow sticky mass, UV 362 nm (76,090/E=870).

(ABCR GmbH) and heated to 90° C. for 20 hours. The cooled solution is washed with moist methanol and concentrated to give 4.2 g of the viscous crude product which, for identification, is chromatographed in hexane/ethyl acetate (in the ratio 19:1) over silica gel. Yield 54% of theory of a yellowish oil, UV 362 nm (E=630).

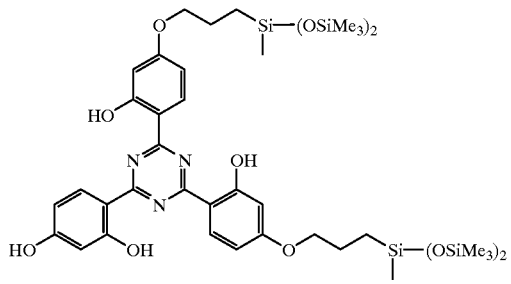

EXAMPLE 3

Introduction of 1,1,1,3,3-pentamethyl-disiloxane into 5,5',5"-tris-allyoxy-2,2',2'-[1,3,5]-triazine-2,4,6-tris-phenol In the same manner as in Example 1, 2.6 g of 5,5'5"-tris-allyloxy-2,2,'2"-[1,3,5]-triazine-2,4,6-triyl-tris-phenol are reacted with 3 equivalents of 1,1,1,3,3-pentamethyl-

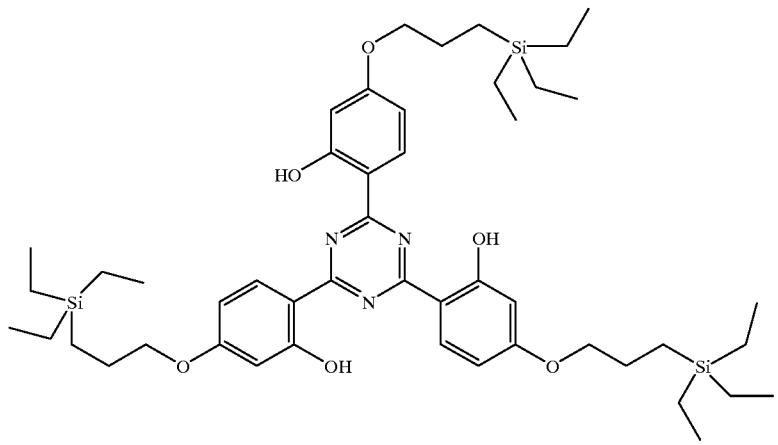

EXAMPLE 2

Introduction of 1,1,1,3,5,5,5-heptamethyl-trisiloxane into 5,5',5"-tris-allyoxy-2,2',2"-[1,3,5]-triazine-2,4,6-triyl-tris-phenol 3.3 g (3 equivalents) of 1,1,1,3,5,5,5-heptamethyl-trisiloxane (Fluka) are added dropwise to a suspension of 2.6 g of 5,5',5"-tris-allyloxy-2,2'2"-[1,3,5]-triazine-2,4,6-triyl-tris-phenol, prepared according to Swiss Patent 484 695, in 40 ml of toluene under Ar protective gas, treated with a few drops of platinum-divinyl-tetramethyl-disiloxane solution disiloxane (Fluka) in place of heptamethyl-trisiloxane for 3 hours at 70° C. and worked-up. The crude product is taken up in methylene chloride, filtered over a wad of silica gel and concentrated. There are obtained 2.8 g of a viscous, clear oil. UV 362 nm (E=808). When the same reaction mixture without toluene as the solvent is treated for 7.5 hours at 80° C. and worked-up in the same manner, then the same product is obtained in 85% yield. The product contains on average 2.55 equivalents of spacer groups.

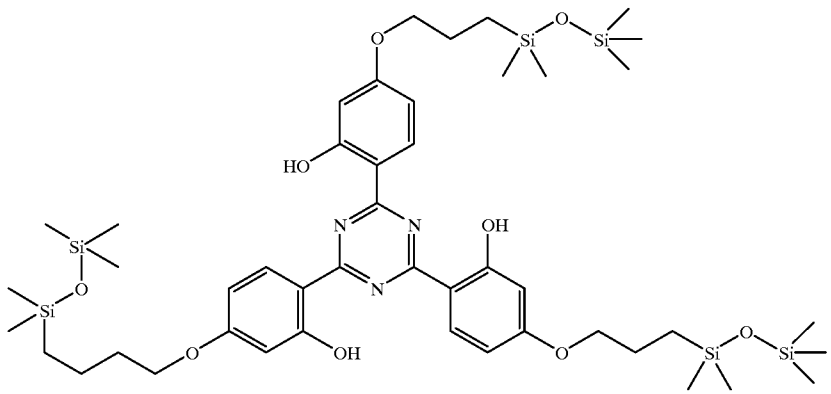

EXAMPLE 4

Introduction of tris-trimethyl-silyloxy-silane into 5, 5',5"-tris-allyloxy-2,2'2"-[1,3,5]-triazine-2,4,6-triyl-tris-phenol In the same manner as in Example 1, 2.6 g of 5,5',5"-tris-allyloxy-2,2',2"-[1,3,5]-triazine-2,4,6-triyl-tris-phenol are reacted with 3 tris-trimethyl-silyloxy-silane (Wacker) in place of heptamethyl-trisiloxane for 6 days under reflux temperature and worked-up. The 4.8 g of crude product obtained are chromatographed in hexane/ethyl acetate in the ratio 19:1 over silica gel. There are obtained 1.9 g of a viscous, sticky mass, UV 360 nm (E =466), and contains 1.9 equivalents of spacer groups.

The same product is obtained when 0.53 g of 5,5',5"-tris-allyloxy-2,2',2"-[1,3,5]-triazine-2,4,6-triyl-tris-phenol and 0.98 g of tris-trimethyl-silyloxy-silane in 9 ml of xylene are treated with 0.02 g of Pt (10%) on active charcoal, refluxed for 6 days and worked-up in the same manner.

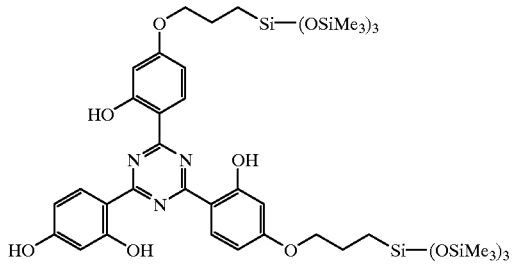

EXAMPLE 5

Introduction of triethoxysilane into 5,5'5"-allyloxy-2,2',2'-[1,3,5]-triazine-2,4,6-triyl-tris-phenol In the same manner as in Example 2, 2.6 g of 5,5',5"-tris-allyloxy-2,2',2"-[1,3,5]-triazine-2,4,6-triyl-tris-phenol are reacted with 3 equivalents of triethoxysilane in place of heptamethyl-trisiloxane for 3 hours at 80° C. and worked-up. A crude yield of 92% is obtained.

This product is chromatographed in hexane/ethyl acetate in the (ratio 9:1). There are obtained 50% of theory of trisubstituted triazine (A), UV 362 nm (E=779, melting point 71–73° C., as well as 17% of theory of disubstituted triazine (B), (UV 360 nm (E8 24) melting point 153–155° C.).

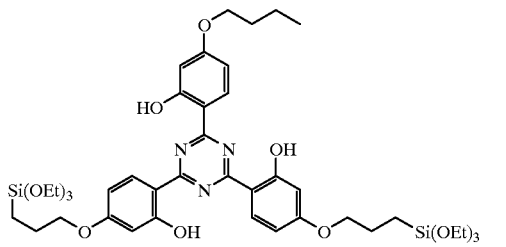

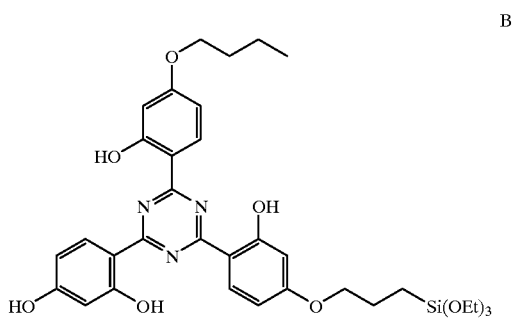

EXAMPLE 6

Introduction of triethylsilane into 5,5',5' tris-propargyloxy-2,2',2"-[1,3,5]-triazine-2,4,6-triyl-tris-phenol a) Preparation of 5,5',5"-tris-propargyloxy-2,2',2"-[1,3,5]-triazine-2,4,6-triyl-tris-phenol:

50 g of 2,4,6-tris-(2,4-dihydroxyphenyl)-1,3,5-triazine (prepared according to Swiss Patent, 484695) and 41.4 g of potassium tert.butylate are suspended in 500 ml of methoxyethanol and treated at 55° C. with 44.3 g of propargyl bromide. The reaction mixture is stirred at this temperature for 2 days, cooled, suction filtered and the filter residue is rinsed with ether. There are obtained 48.6 g (76%) of the desired product, UV 348 nm (E=1123), melting point >240° C.

b) 0.7 g of triethylsilane (Fluka) is added to a suspension of 0.51 g of 5,5',5"-tris-propargyloxy-2,2',2"-[1,3,5]-triazine-2,4,6-triyl-tris-phenol in 18 ml of dimethylformamide under Ar protective gas, treated with a few drops of platinum-divinyl-tetramethyl-disiloxane solution (ABCR GmbH) and heated for 7 hours to 85° C. The cooled solution is partitioned between ethyl acetate and water. The organic phase is filtered over a wad of silica gel and concentrated and gives a resinous mass of the product. UV 352 nm (E=627).

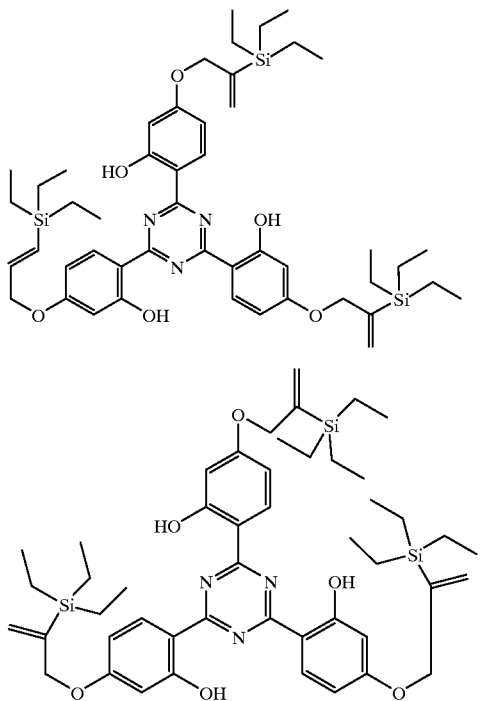

EXAMPLE 7

Introduction of 1,1,1,3,3-pentamethyldisiloxane into 5,5',5",-tris-(but-2-enyl-1-oxy)-2,2',2"-[1,3,5]-triazine-2,4,6-triyl-tris-phenol a) Preparation of 5,5',5"-tris-(but-2-enyl-1-oxy)-2,2',2"-[1,3,5]-triazine-2,4,6-triyl-tris-phenol:

6 g of 2,4,6-tris-(2,4-dihydroxyphenyl)-1,3,5-triazine (prepared according to Swiss Patent 484,695) and 5 g of potassium tert.butylate are suspended in 150 ml of methoxyethanol and treated at 55° C. with 5.4 g of trans-crotyl bromide, heated to 65° C. for about 12 hours, cooled, concentrated and chromatographed in hexane/ethyl acetate (in the ratio 19:1) over silica gel. The front product is isolated. There are obtained 2.1 g (25%) of a yellow powder, UV 362 nm (E=1080), melting point 133–137° C.

b) 0.45 g (3 equivalents) of 1,1,1,3,5,5,5-heptamethyl-trisiloxane (Fluka) is added to a suspension of 0.57 g of 5,5',5"-tris-(but-2-enyl-1-oxy)-2,2',2"-[1,3,5]-triazine-2,4,6-triyl-tris-phenol in 15 ml of toluene under Ar protective gas, treated with a few drops of platinum-divinyl-tetramethyl-disiloxane solution (ABCR GmbH) and heated to 80° C. for about 12 hours. The cooled solution is washed with moist methanol, concentrated and dried in a high vacuum. 0.85 g of a viscous crude product is obtained. This is a mixture with silyl groups substituted at various positions.

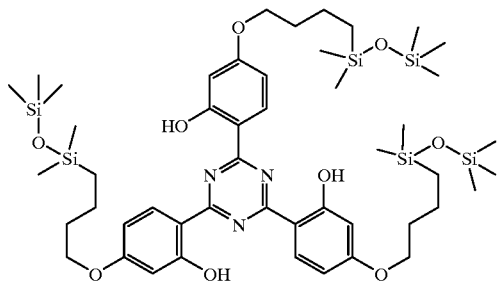

EXAMPLE 8

Introduction of tert.-butyl-dimethylsilane into 5,5',5"-tris-alyloxy-2,2',2"-[1,3,5]-triazine-2,4,6-triyl-tris-phenol In the same manner as in Example 2, 3.9 g of 5,5',5"-tris-allyloxy-2,2',2"-[1,3,5]-triazine-2,4,6-triyl-tris-phenol are reacted with 3 equivalents of tert-butyl-dimethylsilane in place of heptamethyl-trisiloxane and in dichloroethane in place of toluene at 75° C. for 3 days and worked-up. A crude yield of 80% is obtained.

This crude product is chromatographed in hexane/ethyl acetate in the (ratio 9:1). There are obtained 21% of theory of trisubstituted triazine (C), (UV 362 nm (E=801)/melting point 154–157° C.) as well as 46% of theory of disubstituted triazine (D), UV 362 nm (E=885), melting point 143–148° C.

C

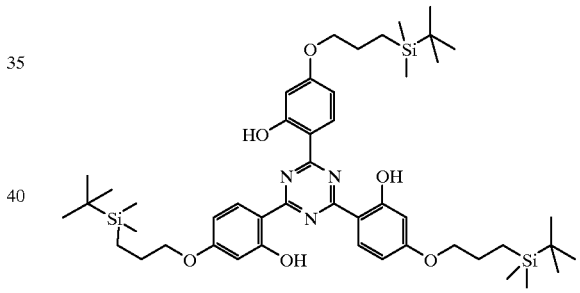

D

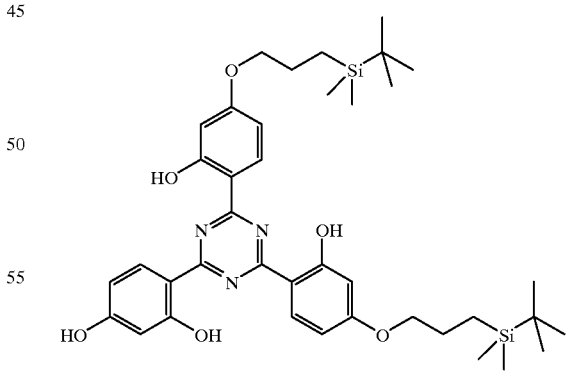

EXAMPLE 9-1

Introduction of 1,1,1,3,3-pentamethyl-disiloxane into 5,5',5"-tris-(pent-4-enyl-1-oxy)-2,2',2"-(1,3,5)triazine-2,4,6-triyl-tris-phenol a) Preparation of 5,5',5"-tris-(pent-4-enyl-1-oxy)-2,2',2"-(1,3,5)triazine-2,4,6-triyl-tris-phenol: 6 g of 2,4,6-tris-(2,4- dihydroxyphenyl)-1,3,5-triazine (prepared according to Swiss Patent 484,695) are suspended in a solution of 2.5 g of potassium tert.butylate in 60 ml of ethanol and treated with 5.3 g of 5-bromo-1-pentene. The clear, orange-red solution is stirred at 70° C. for 72 hours, cooled to 0° C., filtered over a suction filter and rinsed with 150 ml of water and 100 ml of cold ethanol. The filter residue is dried under a high vacuum. 75 g (82%) of a yellow powder are obtained. UV 361 nm (E=1080), melting point 140–143° C.

b) 2.2 g (3 equivalents) of 1,1,1,3,3-pentamethyl-disoloxane (Fluka) are added to a suspension of 3 g of 5,5',5"-tris-(pent-4-enyl-1-oxy)-2,2',2"-(1,3,5)-triazine-2,4,6-triyl-tris-phenol in 40 ml of 1,2-dichlorethane under Ar protective gas, treated with a few drops of platinum-divinyl-tetramethyl-disiloxane solution (ABCR GmbH) and stirred at 70° C. overnight. The cooled solution is poured into 100 ml of water, back-washed twice with 50 ml of dichloromethane and the combined organic phases are concentrated and dried under a high vacuum. 4.9 g of a viscous, yellow-brown crude product are obtained. By chromatography in hexane/ethyl acetate (ratio 95:5) there are obtained 2.65 g of a waxy material with a solubility in Cétinol LC of >35%. UV 362 nm (E=736), melting point 61–63° C.

overnight. Then, the reaction mixture is partitioned between water and $CH_2Cl_2$ and the organic phase is dried over $Na_2SO_4$, concentrated and distilled at 110° C./0.06 mbar. There are obtained 3.8 g of a colourless liquid, the identity of which is confirmed by GC, NMR and MS.

b) Etherification:

0.81 g of 2,4,6-tris-(2,4-dihydroxyphenyl)-1,3,5-triazine are dissolved in a solution of 0.34 g of KOH in 10 ml of ethanol at 60° C. and treated under argon with 1.78 g of 1-(5-bromo-pentyl)-1,1,3,3,3-pentamethyl-disiloxane. The reaction mixture is stirred at 70° C. overnight, treated with 18 ml of tetrahydrofuran and stirred at 70° C. for a further 48 hours. The solution is subsequently partitioned between water and $CH_2Cl_2$, the concentrated organic phase is chromatographed in hexane/EtOAc (97:3–93:7) over silica gel and the front fraction is concentrated. There is obtained 0.75 g of the desired product as a yellowish powder, which is identical with the product from Example 9-1.

EXAMPLE 10

Introduction of 1,1,1,3,3-pentamethyl-disiloxane into 5,5',5'-tris-(but-3-enyl-1-oxy)-2,2',2"-(1,3,5) triazine-2,4,6-triyl-tris-phenol a) Preparation of 5,5',5"-tris-(but-3-enyl-1-oxy)-2,2',2"-(1,3,5)triazine-2,4,6-triyl-tris-phenol: 2,4,6-tris-(2,4-

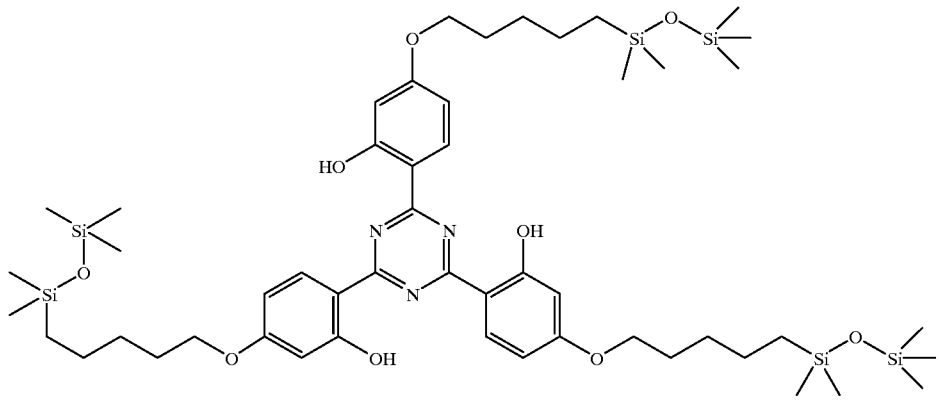

5,5',5"-Tris-[5-(1,1,1,3,3-pentamethyl-disiloxan-oxy)-pentyl-1-oxy]-2,2',2"-(1,3,5)-triazine-2,4,6-triyl-tris-phenol)

EXAMPLE 9-2

Introduction of 1-(5-bromo-pentyl)-1,1,3,3,3-pentamethyl-disiloxane into 2,4,6-tris-(2,4-dihydroxyphenyl)-1,3,5-triazine.

One-step reaction procedure a) Preparation of 1-(5-bromo-pentyl)-1,1,3,3,3-pentamethyl-disiloxane:

2.4 ml of 5-bromo-1-pentene are added under an inert gas to a solution of 3.9 ml of pentamethyl-disiloxane and 0.01 ml of platinum-divinyl-tetramethyl-siloxane complex in 10 ml of 1,2-dichloroethane and the mixture is stirred at 60° C.

dihydroxyphenyl)-1,3,5-triazine is reacted in the same manner as described in Example 9-1a, with 4-bromo-1-butene being used in place of 5-bromo-1-pentene. A pale yellow powder is obtained in 60% yield. UV 361 nm (E=1258), melting point 166–169° C.

b) The material obtained above is reacted with 1,1,1,3,3-pentamethyl-disiloxane (Fluka) in the same manner as described in Example 9-1b. A yellow-green, semi-solid crude product is obtained. By chromatography in hexane/ethyl acetate (ratio 95:5) there is obtained a pale yellow solid with a solubility in Cétinol LC of 8%. UV 362 nm (E=933), melting point 72–75° C.

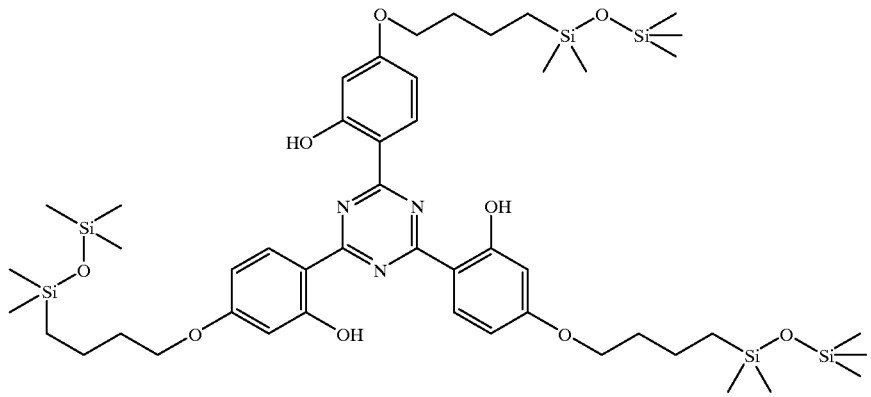

(5,5',5"-Tris-[4-(1,1,1,3,3-pentamethyl-disiloxanoxy)-butyl-1-oxy]-2,2',2"-(1,3,5)-triazine-2,4,6-triyl-tris-phenol)

EXAMPLE 11

Introduction of 1,1,1,3,3-pentamethyl-disiloxane into 5,5',5"-tris-(hex-5-enyl-1-oxy)-2,2',2"-(1,3,5) triazine-2,4,6-triyl-tris-phenol a) Preparation of 5,5',5"-tris-(hex-5-enyl-1-oxy)-2,2',2"-(1,3,5)triazine-2,4,6-tris-phenol: 2,4,6-tris-(2,4-dihydroxyphenyl)-1,3,5-triazine is reacted in the same manner as described in Example 9-1a, with 6-bromo-1-hexene being used in place of 5-bromo-1-pentene. A pale yellow powder is obtained in 79% yield. UV 361 nm (E=1032), melting point 155–158° C.

b) The material obtained above is reacted with 1,1,1,3,3-pentamethyl-disiloxane (Fluka) in the same manner as described in Example 9-1b. A brown, viscous crude product is obtained. By chromatography in hexane/ethyl acetate (ratio 95:5) there is obtained a pale yellow solid. UV 360 nm (E=725).

(5,5',5"n-Tris-[6-(1,1,1,3,3-pentamethyl-disiloxanoxy)-hexyl-1-oxy]-2,2',2"-(1,3,5)-triazine-2,4,6-triyl-tris-phenol)

EXAMPLE 12

Production of an O/W sunscreen lotion UV-A and UV-B: Broad spectrum sunscreen lotion with 3% UV filter from Example 1

Formulation:

| % | Ingredient | Chemical Name |
|---|---|---|
| | | A |
| 6 | Parsol MCX | Octyl methoxycinnamate |
| 3 | Product from Ex. 1 | |
| 10 | Cétiol LC | Coco-caprylate/caprate |
| 4 | Dermol 185 | Isostearyl neopentanoate |
| 0.25 | Diethylene glycol monostearate | PEG-2-stearate |
| 1 | Cetyl alcohol | Cetyl alcohol |
| 0.25 | MPOB/PPOB | Methyl-propylparaben |
| 0.1 | EDTA BD | EDTA Na salt |
| 1 | Amphisol DEA (Giv.) | Diethanolamine |

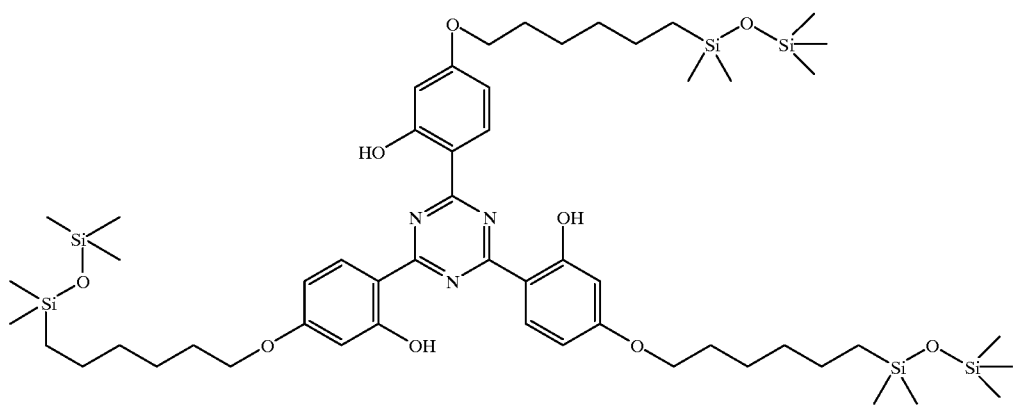

-continued

| % | Ingredient | Chemical Name |
|---|---|---|
| | | B |
| 20 | Permulen TR-1 (+%) | Acrylate C10–C30 alkyl acrylate |
| 48.6 | Deionized water | Aqua |
| 5 | Propylene glycol | 1,2-propanediol |
| 0.8 | KOH (10%) | Potassium hydroxide |

Production: Heating of A to about 85° C. in a reactor, Heating of B to about 85° C. on a hot plate according to the following details Reactor: 250 ml
Batch size 100 g

| Time min | Stirring revolutions minute | Bath °C. | Cooling yes/no | Vacuum yes/no | Product °C. | Remarks and operations |
|---|---|---|---|---|---|---|
| 0 | 200 | 90 | n | n | RT | Part A |
| 25 | 500 | 90 | n | n | 69.5 | Addition of part B, 7.8 ml/min |
| 35 | 500 | 90 | n | n | 84.3 | End of addition |
| 45 | 200 | 20 | y | n | 85.8 | Addition of KOH, cooling |
| 75 | 100 | 20 | y | y | 21.5 | De-gassing |
| 85 | 40 | 20 | y | y | 21 | De-gassing |
| 95 | ~ | ~ | ~ | ~ | 20.9 | End of emulsification |

I claim:

1. A cosmetic composition comprising a compound of the formula:

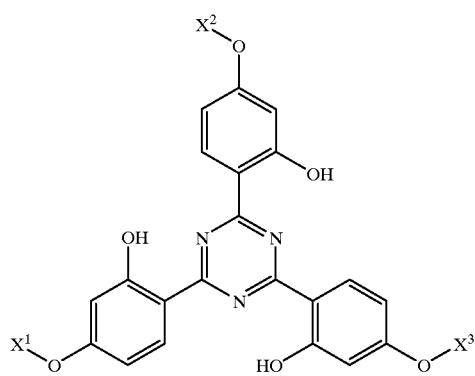

I wherein:
  $X^1$, $X^2$ and $X^3$ are independently —Z—S, or two of $X^1$, $X^2$ and $X^3$ are —Z—S and the third is H or S,
  Z is a saturated or mono- or multipli- unsaturated alkyl group, either linear or branched, having 3–12 carbon atoms, and
  S is tri-$C_{1-6}$-alkyl-silyl, tri-$C_{1-6}$-alkoxy-silyl or triphenyl-silyl, where the $C_{1-6}$-alkyl or $C_{1-6}$-alkoxy groups may be the same or different, or an oligosiloxane having 1–8 silicon atoms 1–8 oxygen atoms and 3–15 carbon atoms.

2. The composition of claim 1 wherein $X^1$, $X^2$ and $X^3$ are —Z—S.

3. The composition of claim 2 wherein $X^1$, $X^2$ and $X^3$ are all the same.

4. The composition of claim 3 wherein Z is 3-propyl, 2-propyl, 3-propenyl, 2-propen-3-yl, 2-propen-2-yl, 2-methyl-2-propyl, 2-methyl-3-propenyl, 4-butyl, 3-butyl, 2-butyl, 3-butenyl, 3-methyl-2-butyl, 2,4-pentadien-5-yl, 4-pentyl, 5-pentyl, 5-hexyl, 6-hexyl or 2-dodecen-12-yl.

5. The composition of claim 4 wherein S is $SiMe_3$, $SiEt_3$, $SiMe_2$ethyl, Si(n-propyl)$_3$, Si(isopropenyl)$_3$, Si(tert. butyl)$_3$, Si(sec. butyl)$_3$, $SiMe_2$tert.butyl, $SiMe_2$sec.butyl, $SiMe_2$thexyl, (thexyl is 1,1,2-trimethylpropyl), Si(OMe)$_3$, Si(OEt)$_3$, or Si(OPh)$_3$.

6. The composition of claim 5 wherein Z is 3-propyl, 3-propenyl, 2-propen-2-yl, 4-butyl, 5-pentyl, or 6-hexyl, and S is $SiEt_3$, $SiMe_2$ethyl, Si(n-propyl)$_3$, $SiMe_2$tert.butyl, $SiMe_2$thexyl, or Si(OEt)$_3$.

7. The composition of claim 6 having the formula:

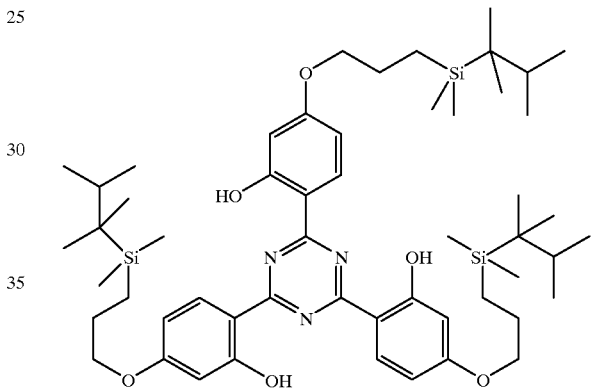

8. The composition of claim 6 having the formula:

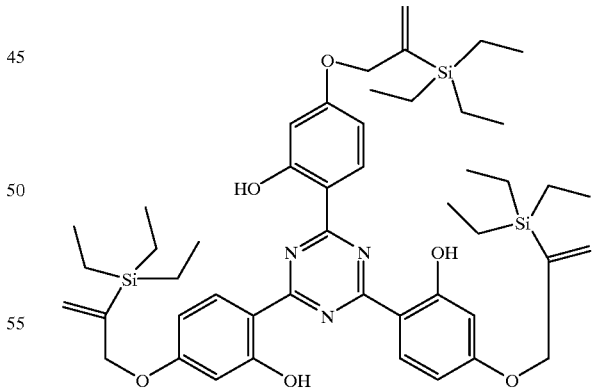

9. The composition of claim 6 having the formula:
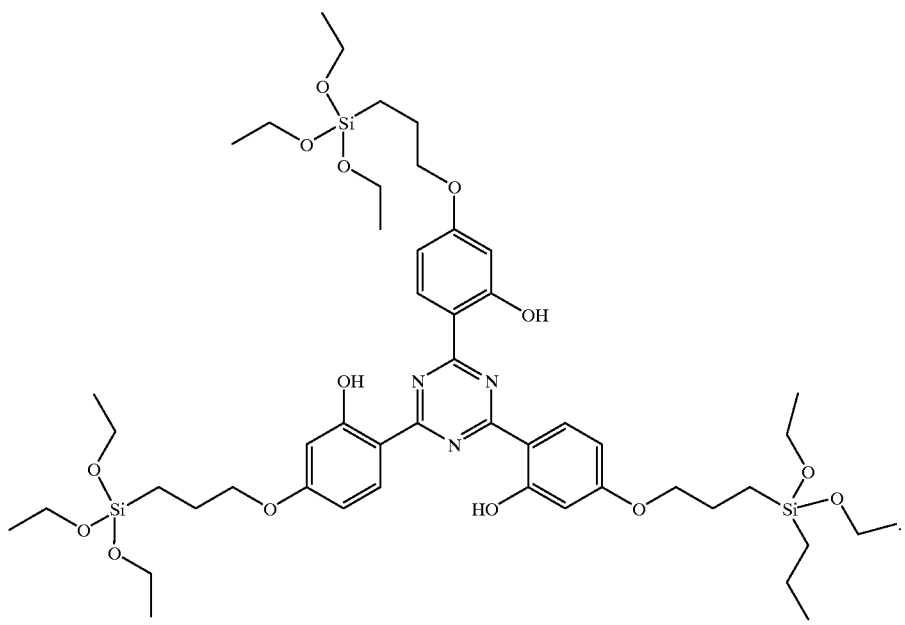
10. The composition of claim 6 having the formula:
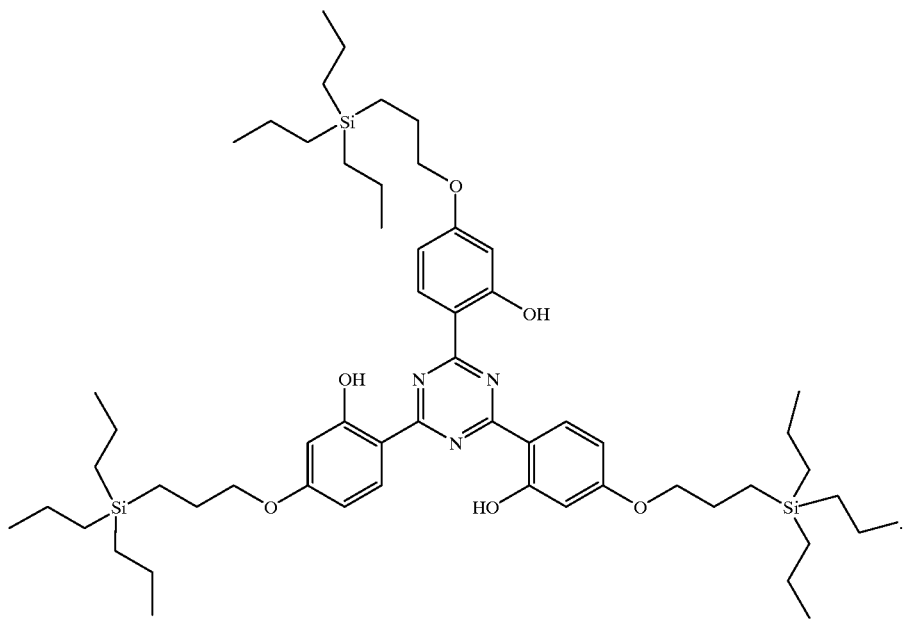
11. The composition of claim 6 having the formula:

12. The composition of claim 6 having the formula:
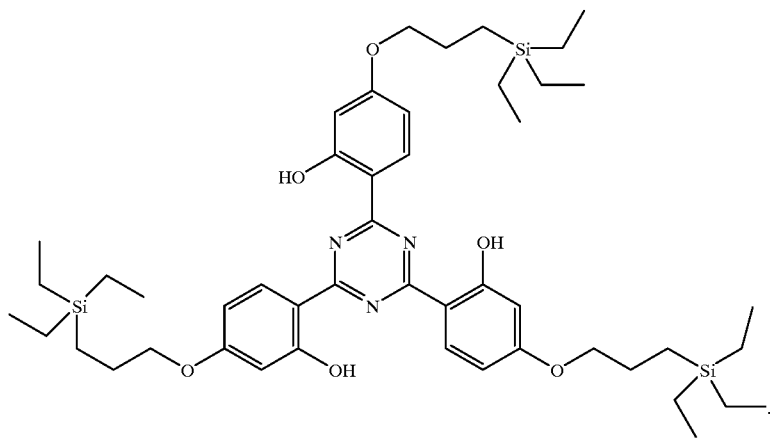
13. The composition of claim 6 having the formula:
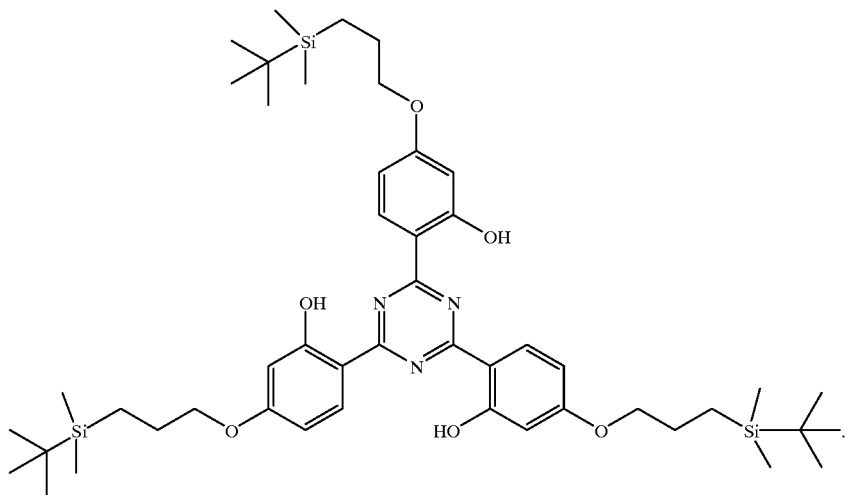
14. The composition of claim 6 having the formula:
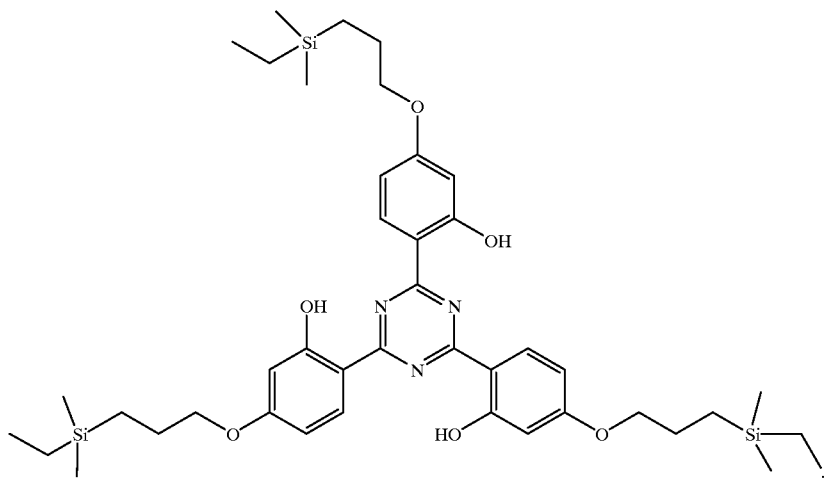

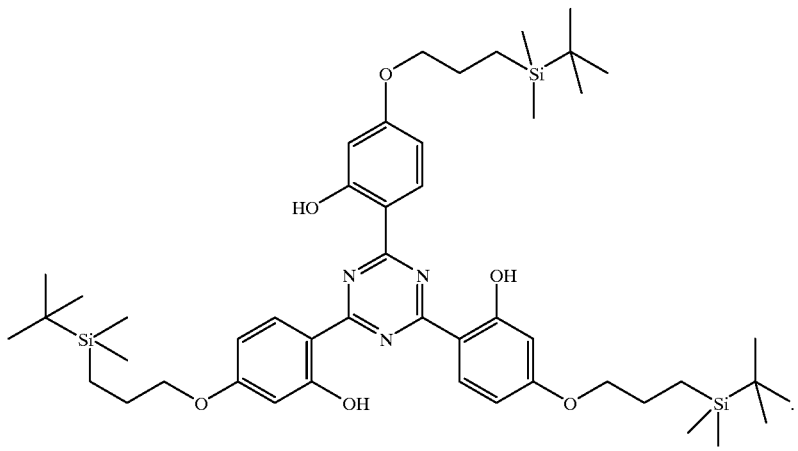

15. The composition of claim 2 wherein two of the three groups $X^1$, $X^2$ and $X^3$ are the same and are different from the third group.

16. The composition of claim 15 wherein Z is 3-propyl, 2-propyl, 3-propenyl, 2-propen-3-yl, 2-propen-2-yl, 2-methyl-2-propyl, 2-methyl-3-propenyl, 4-butyl, 3-butyl, 2-butyl, 3-butenyl, 3-methyl-2-butyl, 2,4-pentadien-5-yl, 4-pentyl, 5-pentyl, 5-hexyl, 6-hexyl or 2-dodecen-12-yl.

17. The composition of claim 16 wherein S is $SiMe_3$, $SiEt_3$, $SiMe_2ethyl$, $Si(n-propyl)_3$, $Si(isopropenyl)_3$, $Si(tert. butyl)_3$, $Si(sec. butyl)_3$, $SiMe_2tert.butyl$, $SiMe_2sec.butyl$, $SiMe_2thexyl$, $Si(OMe)_3$, $Si(OEt)_3$, or $Si(OPh)_3$.

18. The composition of claim 17 wherein Z is 3-propyl, 3-propenyl, 2-propen-2-yl, 4-butyl, 5-pentyl, or 6-hexyl, and S is $SiEt_3$, $SiMe_2ethyl$, $Si(n-propyl)_3$, $SiMe_2tert.butyl$, $SiMe_2thexyl$, or $Si(OEt)_3$.

19. The composition of claim 18 of the formula:

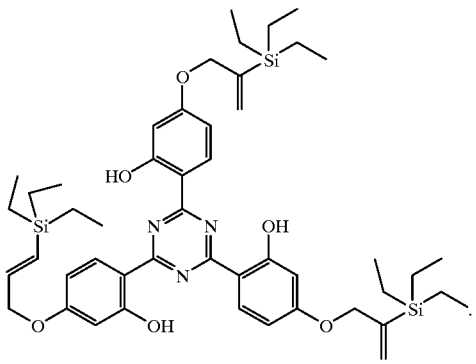

20. The composition of claim 4 wherein S is an oligosiloxane.

21. The composition of claim 20 wherein S is a group of the formula:

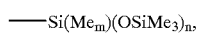
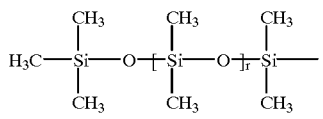

or

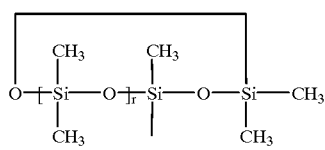

wherein m=0, 1 or 2, n=3, 2 or 1 and m+n =3, and r is an integer from 0 to 6.

22. The composition of claim 21 wherein Z is 3-propyl, 3-propenyl, 2-propen-2-yl, 4-butyl, 5-pentyl, or 6-hexyl, and S is $Si(O-SiMe_3)_3$, $Si(Me)(O-SiMe_3)_2$ or $Si(Me)_2(O-SiMe_3)$.

23. The composition of claim 22 having the formula:

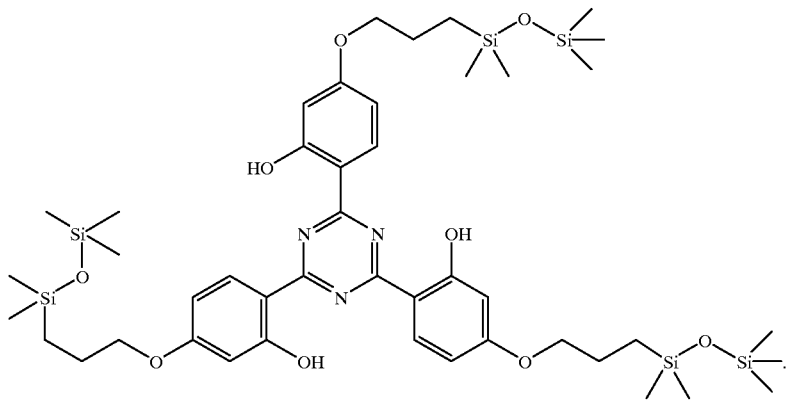
24. The composition of claim 22 having the formula:
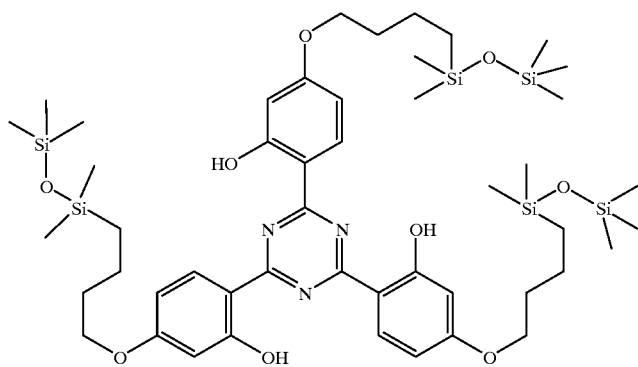
25. The composition of claim 22 having the formula:
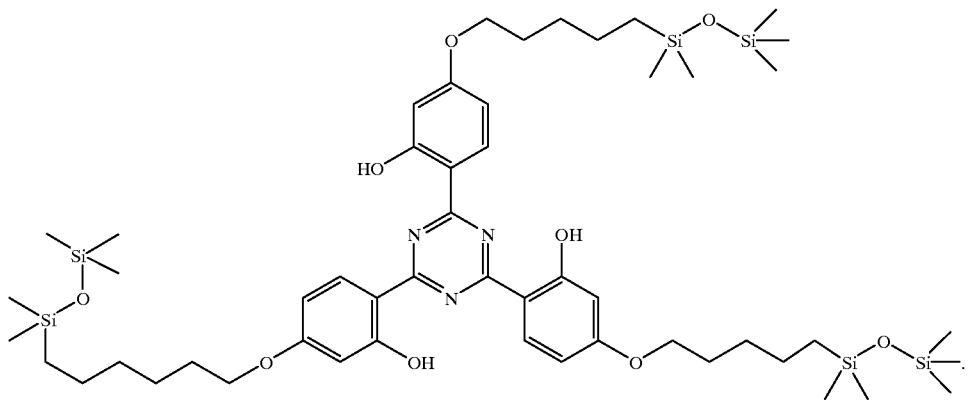
26. The composition of claim 22 having the formula:

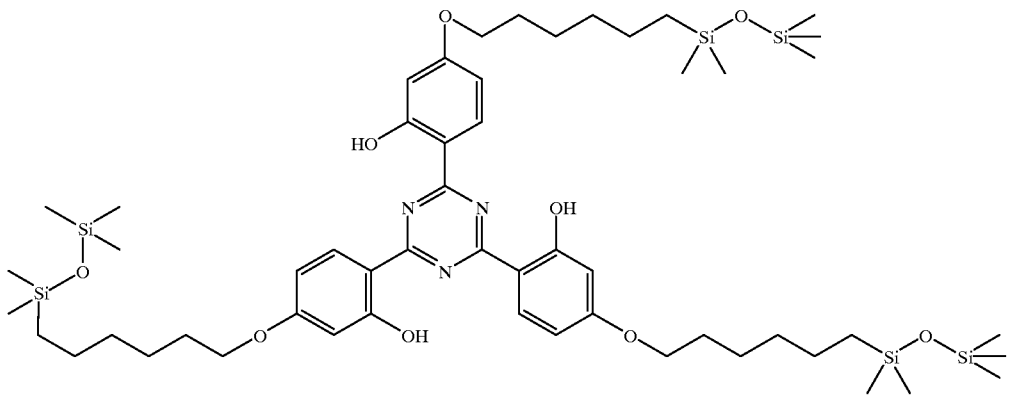

27. The composition of claim 1 wherein two of $X^1$, $X^2$ and $X^3$ are —Z—S and the remaining group is hydrogen or S.

28. The composition of claim 27 wherein two of $X^1$, $X^2$ and $X^3$ are —Z—S and the remaining group is S.

29. The composition of claim 28 wherein the —Z—S groups are the same.

30. The composition of claim 29 wherein Z is 3-propyl, 2-propyl, 3-propenyl, 2-propen-3-yl, 2-propen-2-yl, 2-methyl-2-propyl, 2-methyl-3-propenyl, 4-butyl, 3-butyl, 2-butyl, 3-butenyl, 3-methyl-2-butyl, 2,4-pentadien-5-yl, 4-pentyl, 5-pentyl, 5-hexyl, 6-hexyl or 2-dodecen-12-yl, preferably 3-propyl, 4-butyl or 5-pentyl.

31. The composition of claim 30 wherein S is $SiMe_3$, $SiEt_3$, $SiMe_2$ethyl, $Si(n-propyl)_3$, $Si(isopropenyl)_3$, $Si(tert.$ $butyl)_3$, $Si(sec. butyl)_3$, $SiMe_2tert.butyl$, $SiMe_2sec.butyl$, $SiMe_2thexyl$, (thexyl is 1,1,2-trimethylpropyl), $Si(OMe)_3$, $Si(OEt)_3$, or $Si(OPh)_3$.

32. The composition of claim 31 wherein Z is 3-propyl, 3-propenyl, 2-propen-2-yl, 4-butyl, 5-pentyl, or 6-hexyl, and S is $SiEt_3$, $SiMe_2$ethyl, $Si(n-propyl)_3$, $SiMe_2tert.butyl$, $SiMe_2thexyl$, or $Si(OEt)_3$.

33. The composition of claim 27 wherein two of $X^1$, $X^2$ and $X^3$ are —Z—S and the remaining group is hydrogen.

34. The composition of claim 33 wherein the —Z—S groups are the same.

35. The composition of claim 34 wherein Z is 3-propyl, 2-propyl, 3-propenyl, 2-propen-3-yl, 2-propen-2-yl, 2-methyl-2-propyl, 2-methyl-3-propenyl, 4-butyl, 3-butyl, 2-butyl, 3-butenyl, 3-methyl-2-butyl-2,4-pentadien-5-yl, 4-pentyl, 5-pentyl, 5-hexyl, 6-hexyl or 2-dodecen-12-yl.

36. The composition of claim 35 wherein S is $SiMe_3$, $SiEt_3$, $SiMe_2$ethyl, $Si(n-propyl)_3$, $Si(isopropenyl)_3$, $Si(tert.$ $butyl)_3$, $Si(sec. butyl)_3$, $SiMe_2tert.butyl$, $SiMe_2sec.butyl$, $SiMe_2thexyl$, $Si(OMe)_3$, $Si(OEt)_3$, or $Si(OPh)_3$.

37. The composition of claim 36 wherein Z is 3-propyl, 3-propenyl, 2-propen-2-yl, 4-butyl, 5-pentyl, or 6-hexyl, and S is $SiEt_3$, $SiMe_2$ethyl, $Si(n-propyl)_3$, $SiMe_2tert.butyl$, $SiMe_2thexyl$, or $Si(OEt)_3$.

38. The composition of claim 37 having the formula:

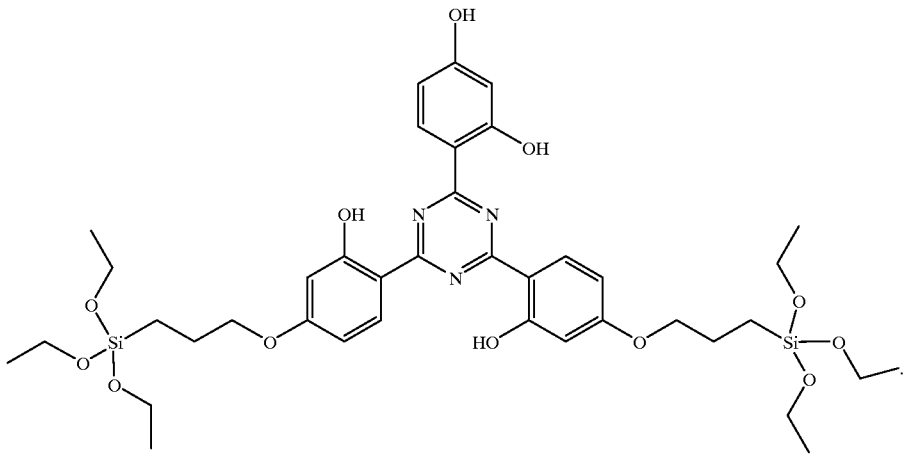

39. The composition of claim 37 having the formula:

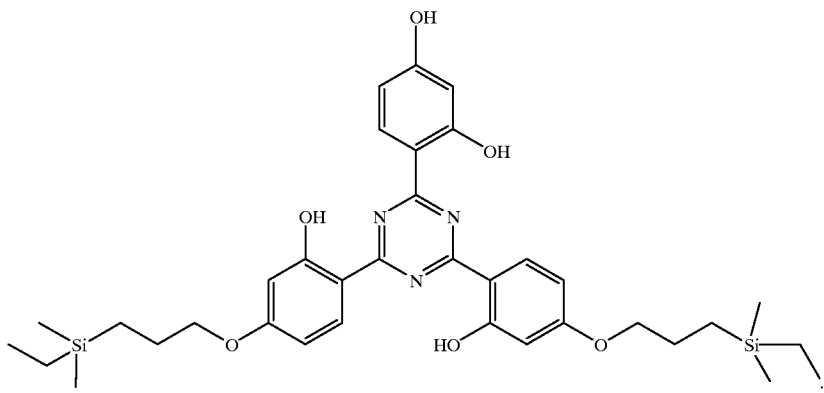

40. The composition of claim 37 having the formula:

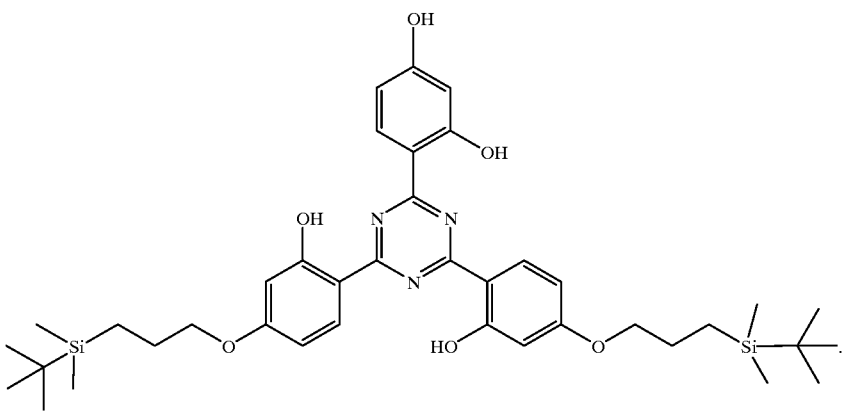

41. The composition of claim 35 wherein S is an oligosiloxane.

42. The composition of claim 41 wherein S is a group of the formula:

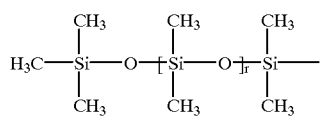

or

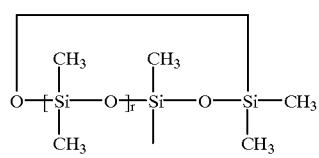

wherein m=0, 1 or 2, n=3, 2 or 1 and m+n =3, and r is an integer from 0 to 6.

43. The composition of claim 42 wherein Z is 3-propyl, 3-propenyl, 2-propen-2-yl, 4-butyl, 5-pentyl, or 6-hexyl, and S is Si(O—SiMe$_3$)$_3$, Si(Me)(O—SiMe$_3$)$_2$ or Si(Me)$_2$(O—SiMe$_3$).

44. The composition of claim 43 having the formula:

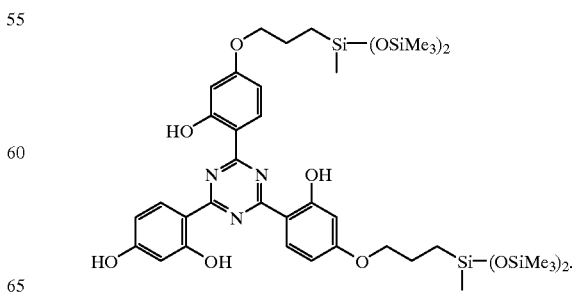

45. The composition of claim 43 having the formula:

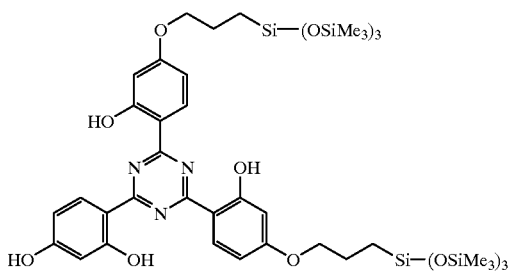

46. The composition of claim 1, further comprising a cosmetic solvent.

47. The composition of claim 1, further comprising a UV filter.

48. The composition of claim 47, wherein the UV filter is a UV-B filter.

49. The method of using the cosmetic composition of claim 1 as a cosmetic light screening composition.

50. The composition of claim 4, wherein Z is 3-propyl, 4-butyl or 5-pentyl.

51. The composition of claim 16, wherein Z is 3-propyl, 4-butyl or 5-pentyl.

52. The composition of claim 35, wherein Z is 3-propyl, 4-butyl or 5-pentyl.

* * * * *

UNITED STATES PATENT AND TRADEMARK OFFICE
CERTIFICATE OF CORRECTION

PATENT : 5,976,512
DATED : November 2, 1999
INVENTOR(S): Ulrich Huber

It is certified that error appears in the above-identified patent and that said Letters Patent is hereby corrected as shown below:

Claim 42, column 39, line 48, insert -- $-Si(Me_m)(OSiMe_3)n,$ --.

Signed and Sealed this

Fifteenth Day of May, 2001

*Attest:*

NICHOLAS P. GODICI

*Attesting Officer*  *Acting Director of the United States Patent and Trademark Office*